United States Patent [19]

Groitzsch et al.

[11] Patent Number: 4,938,901

[45] Date of Patent: Jul. 3, 1990

[54] PROCESS OF MAKING A SURGICAL SPONGE CONTAINING AN X-RAY CONTRAST AGENT

[75] Inventors: Dieter Groitzsch, Hirschberg; Bernhard Klein, Birkenau-Löhrbach; Gerhard Schaut, Hemsbach, all of Fed. Rep. of Germany

[73] Assignee: Firma Carl Freudenberg, Weinheim, Fed. Rep. of Germany

[21] Appl. No.: 240,254

[22] Filed: Sep. 2, 1988

Related U.S. Application Data

[62] Division of Ser. No. 101,972, Sep. 28, 1987, abandoned.

[30] Foreign Application Priority Data

Dec. 2, 1986 [DE] Fed. Rep. of Germany ....... 3641151

[51] Int. Cl.⁵ .................. B29C 35/08; B29C 47/06; B32B 23/02; B32B 23/04
[52] U.S. Cl. ......................... 264/22; 264/101; 264/156; 264/171; 264/177.1; 264/236; 604/362; 604/365; 604/374
[58] Field of Search ................. 264/22, 87, 101, 171, 264/177.1, 236, 154, 156; 604/362, 265, 369, 374

[56] References Cited

U.S. PATENT DOCUMENTS

| 3,133,538 | 5/1964 | Pratt et al. | 604/362 |
| 3,566,871 | 3/1971 | Richter et al. | 604/362 |
| 3,840,013 | 10/1974 | Mesek et al. | 604/365 |
| 3,911,922 | 10/1975 | Kliger | 604/362 |
| 3,935,863 | 2/1976 | Kliger | 604/369 |
| 3,961,629 | 6/1976 | Richter et al. | 604/369 |
| 3,965,907 | 6/1976 | Hardy et al. | 604/362 |
| 3,977,406 | 8/1976 | Roth | 604/362 |
| 4,068,666 | 1/1978 | Shiff | 604/374 |
| 4,639,253 | 1/1987 | Dyer et al. | 604/362 |
| 4,645,499 | 2/1987 | Rupinskas | 604/362 |
| 4,718,897 | 1/1988 | Elves | 604/362 |

FOREIGN PATENT DOCUMENTS

| 961247 | 1/1975 | Canada | 604/362 |
| 160560 | 11/1985 | European Pat. Off. | 604/362 |
| 2600185 | 7/1976 | Fed. Rep. of Germany . | |
| 839451 | 6/1960 | United Kingdom | 604/362 |
| 884143 | 12/1961 | United Kingdom | 604/362 |
| 2069842 | 9/1981 | United Kingdom . | |

Primary Examiner—Jeffery Thurlow
Assistant Examiner—Leo B. Tentoni
Attorney, Agent, or Firm—Felfe & Lynch

[57] ABSTRACT

Disclosed is a process for producing a surgical sponge which contains contrast agent embedded in a polymer matrix in proportions of up to 70 wt. %. The matrix consists of a polymer material free of plasticizers. In the process for the production of the sponge a matrix for the contrast agent is used, which is an uncrosslinked, viscous liquid, prepolymer state until after it has been extruded onto the basic fleece material, and not until a process step that then follows is the polymerization completed.

11 Claims, 1 Drawing Sheet

PROCESS OF MAKING A SURGICAL SPONGE CONTAINING AN X-RAY CONTRAST AGENT

This is a Divisional of Application Ser. No. 101,972, filed Sep. 28, 1987, now abandoned.

BACKGROUND OF THE INVENTION

The present invention is in a surgical sponge or compress and a process for the manufacture thereof. The surgical sponge is made from a fleece consolidated by intertangling fibers or by fusion, from a majority of cellulosic fibers, with an X-ray contrast medium autogenously and irremovably fastened thereto, which consists of a polymeric synthetic matrix filled with a material impermeable to X-rays, into which at least some of the fleece fibers adjacent to it are embedded, and which contains absorbent material in amounts of at least 40 weight-percent.

After surgical intervention, it is necessary to make certain that every such sponge or compress is removed from the patient's body. It is therefore common practice to provide these materials with color identification that clearly distinguishes them from the color of blood, by using, for example, blue or green dyed filaments. The dyes can also be made reflective, phosphorescent, fluorescent or iridescent.

In spite of all precautions, however, it is not always possible to prevent sponge material from being accidentally left in the site of the operation. If a patient is having unusual post-operation discomfort, it must be determined whether the discomfort is caused by any overlooked sponge material. It is therefore necessary to provide surgical sponges at certain points with materials or embedments which are impermeable to X-rays, and which can be detected as shadows in the X-ray photograph in case of doubt, and thus permit positive detection. The X-ray impermeable material is generally barium sulfate in particle form.

EP-A No. 160,560 describes a surgical sponge of nonwoven material containing no binding agent and consolidated and perforated by high-pressure water jets, in whose interior at least one X-ray-absorbent element (X-ray contrast medium) is situated between the fiber layers as an integral component of the sponge.

This element is held in position by entangling fibers. The X-ray contrast medium preferably consists of at least one yarn, fiber ribbon or endless monofilament with a polymeric, thermoplastic matrix which contains barium sulfate embedded in amounts of approximately 60 weight-percent. The matrix is partially thermally bound to the surrounding nonwoven fibers, i.e., the fibers are embedded in the matrix softened afterward by hot compression, and thus they fix the monofilament or yarn in place.

The nonwovens can consist of natural or synthetic randomly laid fibers or mixtures thereof. The matrix of the X-ray contrast medium preferably consists of polyvinyl chloride in the case of monofilaments, has a diameter of about 0.6 mm, and in addition to the barium sulfate, contains pigments which are of a color that contrasts clearly with that of blood. In any case, however, it must have thermoplastic properties in order to be fused afterward to the surrounding fibers.

The arrangement of a number of X-ray contrast filaments in patterns or rows, and the number thereof, depends on the size and folding with which the sponge is to be used. It must only be assured that each sponge ready for use contains a sufficient number of contrast threads. Fragments of filaments can also be incorporated. Any sponge that might be erroneously left in the wound is distinguished by its patterned or interrupted arrangement from any suture material also containing contrast agents which must necessarily be left in the body.

DE-OS No. 26 00 185 discloses a process in which a surgical sponge is made with an insert intimately and permanently bonded to the fibers by extruding a melted filament of X-ray impermeable, thermoplastic material onto a moving, absorbent fabric, and pressed in the still tacky state against the fabric. A compressed strand is thus formed with surrounding fibers embedded therein. Subsequent remelting of the thermoplastic material is not necessary. No guide for the selection of appropriate thermoplastic polymers is given.

The known sponges have a number of product-related and also process-related disadvantages. For instance, the clarity of the contrast on the X-ray photograph depends on the amount of the applied contrast medium, the density (percentage content) of the X-ray contrast particles and the radiation dose. To minimize the exposure of the human body to radiation it is desirable to maintain the radiation dose as low as possible. It is also desirable to have the highest possible content of contrast agent in the polymer matrix, such as 60 weight-percent and more.

Inorganic particles, usually barium sulfate, incorporated into the matrix in the said amounts produce a drastic hardening and reduction of the flexibility in the thermoplastic matrix. The effect of the hardening is so pronounced that, for example, a contrast filament according to DE-OS No. 26 00 185 or with a PVC matrix according to EP-A No. 160 560 cannot be at all satisfactorily extruded (spun) unless the plasticizer content is unusually high. Consequently, those matrix materials which cannot be mixed with plasticizers or which are rendered inherently soft only by copolymerization must not be used in making X-ray contrast monofilaments with large proportions of barium sulfate filler.

Even the thermoplastics which can be treated with plasticizers which are essential to them have disadvantages in applications in surgical sponges since plasticizers diffuse, or migrate, within the nonwoven and therefore can have a toxic effect in contact with wounds.

In the interest of achieving more reliable detection, the above-cited applications propose the thermal fixation of X-ray contrast fibers which are relatively thick (0.64 mm) over their entire length, while or after they are deposited. Experience shows, however, that, there is a considerable impairment or even prevention of the (multiple) folding of the sponge due to the thickness of the filament. Mere spot-fixation, however, does not suffice to reliably fix the contrast filaments because filling the matrix with a large proportion of contrast agent considerably impairs its adhesiveness in the heat-softened state.

Gauze or nonwoven gauze substitutes are normally supplied unsterilized and are sterilized in hospital steam sterilizers by the pulsating pressure-vacuum principle at 134° C. in the autoclave. Hot steam sterilization is possible, for example, with cotton-containing fabrics or nonwovens. However, there is a danger that the layered and folded pads may stick together after steam sterilization if the matrix of the X-ray contrast medium consists of thermoplastic polymers with added plasticized polymers.

An object of the present invention is to overcome the above described disadvantages by providing an improved surgical sponge, and a novel method of producing it. The polymer matrix of the contrast medium must therefore be free of plasticizers and yet soft, flexible and resilient, and must be capable of withstanding hot steam sterilization without softening. It must nevertheless be easily extrudable even with high contents of contrast agent. The fixation of the X-ray contrast medium in the still adhesive state directly after extrusion must be possible in an autogenous and permanent manner in or on the nonwoven material of the sponge, without impairing the ability of the sponge to be repeatedly folded.

The term, "X-ray contrast medium", as used herein will be understood to mean any kind of incorporation of a substance absorbing X-rays, usually barium sulfate, into the polymer matrix. The system can have any desired geometrical shape. Furthermore, it is desirable to distribute a relatively large number of contrast media in, or on, the nonwoven fabric in order to assure reliable detection with X-rays.

SUMMARY OF THE INVENTION

The above-described disadvantages are avoided and stated objects achieved by a surgical sponge of the invention as well as the inventive process for its manufacture.

The sponge of the present invention is a surgical sponge of a consolidated fleece from a majority of cellulosic fibers, with an X-ray contrast agent medium bounded thereto. The fleece consolidation is by intertangling fibers or by fusion. The contrast medium consists of a polymeric synthetic matrix filled with a material impermeable to X-rays into which at least some of the adjacent fleece fibers are embedded and which contains the absorbent material in an amount of at least 40 wt.-%. The synthetic matrix consists of a polymer material free of external plasticizers and has soft, resilient and flexible properties.

The matrix of the X-ray contrast medium is, according to the invention, free of external plasticizers, and soft, resilient and flexible.

Preferably, but due to the small percentage in the absorbent sponge base, not necessarily, the matrix material can be absorbent. For greater mechanical strength, however, moisture-repellent polymeric matrices can also be used, without the anticipated disadvantages, inasmuch as then the sponge according to the invention can be easily autoclaved without softening. The X-ray contrast medium according to the invention is sufficiently soft, flexible and resilient so as not to interfere with the folding of the sponge.

The matrix material is a crosslinked acrylate polymer or a linear or crosslinked polyurea, a polyurethane polyurea, or a mixture of both. These substances can be made from prepolymers which complete their reaction with water and thus make possible an especially simple manufacturing process as discussed below. Additional advantages reside in the special softness and flexibility of this class of plastics, not showing a significant softening behavior during steam sterilization.

For easy identification, even in deeper layers of the tissue of the human body, the polymer matrix should contain 40 to 70% by weight of contrast agents, preferably barium sulfate particles.

The X-ray contrast medium can be of any desirable form. In order to be reliably detectable by X-rays, a preferred form, in many cases, is a monofilament of circular cross section having a diameter of 0.2 to 0.5 mm or a titer of 150 to 700 tex.

The contrast medium, which is fused to adjacent fibers, lies on the surface of the nonwoven. By appropriate folding it is thus possible that portions of the contrast medium or media will be situated on the side facing the X-ray detector and will thus be easily detected regardless of the sponge's position in an operation wound. The risk that particles may become loose during use is minimal because they are so firmly bonded to the nonwoven fibers.

To distinguish the contrast agent in some overlooked sponge from contrast agent containing suture material which must necessarily remain in the wound, it is advantageous to arrange the contrast medium in distinguishable patterns or rows.

The contrast medium according to the invention is preferably treated with blue or green coloring in the form of pigments or solutions, which can also be phosphorescent. A so treated sponge will always be strikingly visible during treatment of the wound, and even after heavy absorption of blood.

The sponge according to the invention may be perforated or unperforated and/or can be patterned by hot embossing. It may consist of the known fibers or fiber mixtures that have been found desirable for these products. In the interest of absorptivity, preference is given to a predominant amount—i.e., around 70% by weight—of cellulosic fibers, such as spun rayon, cotton, cellulose, or mixtures thereof. The remainder of the fiber materials are then, for example, polyacrylonitrile hollow fibers, fully synthetic heterofil fibers, polyamides, polyesters and polyolefins, or mixtures thereof. Also usable are nonwoven fabrics free of external binding agents and built up in three layers, each with a very light outer layer of autoclavable, thermoplastic synthetic fibers and a relatively heavy absorbent middle layer, which have very little tendency to stick to the wound since they have thermally smoothed surfaces.

The weight of the unfolded sponge material per unit area is about 30 to 100 grams per square meter, the lighter varieties being preferred.

The binding of the X-ray contrast medium into the fiber sandwich is so effective in every embodiment of the present invention that the matrix need not be additionally spot-bonded to the nonwoven base.

According to the process of the invention, the matrix which is treated with a sufficient amount of X-ray contrast agent, usually barium sulfate, is not a thermoplastic polymer but a reactive, low-melting prepolymer which contains no plasticizer whatever. This prepolymer has chemically reactive groups.

Preferably the prepolymers have two to five terminal isocyanate groups which can react with water in excess as reagent, to form urea. The molecular weight of the urethane prepolymers is preferably between 164 and 20,000. Molecular weights between 1200 and 8000 have been found to be especially advantageous. Lower weights result in relatively stiff products, and weights above 8000, as a rule, make fabrication difficult because the viscosity of the prepolymer can attain excessively high levels.

The above-stated content of two to five free isocyanate groups should not be exceeded, so as to avoid excessive foaming in the reaction by the evolution of carbon dioxide. This must be taken into account especially when the weight of the sponge is relatively low, e.g., 35 to 40 g/m$^2$.

Water is especially preferred as one of the reactants, because it is inexpensive, readily available, sufficiently reactive, and, above all, can form urea. The polyurea structure is especially preferred due to its thermal stability during steam sterilization.

Basically any difunctional and polyfunctional isocyanate can be used. Aliphatic diiso- and triisocyanates, such as for example hexamethylene diisocyanate and a trifunctional isocyanate based on a biuret structure from hexamethylene diisocyanate with a molecular weight of 478 are highly preferred for the field of surgery.

The polyether and/or polyester polyols known from polyurethane chemistry can be used as soft components. Examples are polypropylene oxide diol (molecular weight about 3600), polytetrahydrofurandiol (molecular weight about 200) or polyesters of adipic acid with butanediol (molecular weight about 2000).

To adapt the reactivity of the isocyanates to the process conditions, if necessary, the known catalysts for polyurethane can be used, such as tertiary amines, (cyclo)aminoethers and amidines, salts of weak organic acids, metal organic compounds and N-acylated amines. It is also known that mixtures of two different catalysts such as amines and metal organic compounds provide a synergistic effect (Kunststoff-Handbook 7, Polyurethane, Carl Hanser Verlag Munchen Wien, 1983 pages 92–96).

The curing of the prepolymer does not take place until after the extrusion, i.e, after the development of the geometrical shape, and after adherence to the fleece fibers of the sponge and the incorporation of the adjacent fibers.

If chemical curing is not desired, one can use oligomeric organic acrylate prepolymers which can be crosslinked by particle beams or wave beams, with the addition, if necessary, of initiator substances. Examples are oligomeric systems composed of epoxide/acrylate, polyester/urethane/acrylate, polyether/acrylate or polyester acrylate. Here again, it is to be noted that the crosslinked products have soft, resilient and flexible properties. In crosslinking with low-energy radiation (e.g., ultraviolet rays) it must also be assured that they also penetrate through the fiber substrate into the matrix substance.

Even when the contrast agent contents amount to 40 to 70% by weight, and at temperatures definitely below 80°C., the prepolymer's viscous-fluid consistency enables it to become immediately and intensively bonded to the adjacent fibers upon contact with the sponge substrate. After curing, this bond is strong enough to fix the contrast medium permanently. Additional tacking, e.g., spot tacking, of the matrix is unnecessary.

The prepolymer can be treated with a solvent to reduce its viscosity. This, however, is not advantageous, for economical reasons, because the solvent would have to be removed and regenerated after the X-ray contrast medium has been incorporated. Solvent-free systems, however, have proven advantageous.

The plasticizer-free, viscous liquid prepolymers of the matrix substance of the contrast agent according to the invention combine the advantage of a fluid substance able to contain large amounts of contrast agent, with the advantage of spun rayon, namely, of being steam-sterilizable at temperatures of about 134° C.

There is no need to choose absorbent or absorbentized prepolymers to favor greater mechanical strength, since the ability to absorb moisture is already assured by the very high weight proportion of the base fleece material.

The contrast medium can be incorporated in the prepolymer state at any stage of the manufacture of the sponge. It is possible, for example, to perform this step during the folding process of the fleece material (packaged) into a layered, ready-for-use sponge, and then to crosslink.

Matrix prepolymers which can be crosslinked with water are especially useful in modern, fleece consolidating processes which, instead of using binding agent, utilize high-energy water jets for mechanical intertangling of fibers. The same advantages exist if only a perforation without intertangling is performed with low-energy water jets. In either case, after removal of excess water, the residual moisture can be used directly to cure the plastic matrix. This constitutes an especially economical method. Also, the carbon dioxide cleavage product is not toxic.

Another advantage of the water-reactive prepolymers is that, even when the fleece is relatively thick, the water reliably penetrates the fleece layer because of the large proportion of absorbent fibers, and contacts any prepolymer present within it.

The X-ray contrast medium is preferably extruded in the form of an endless monofilament. Its diameter is preferably between 0.2 and 0.5 mm. The extrusion is commonly performed through spinnerets containing circular holes in one or more rows, through which the filled prepolymer is forced. The number and spacing of the holes are to be selected such that, after the finished sponge material has been cut and folded, at least one contrast monofilament will be contained in each sponge.

Folded compresses are commonly supplied in the sizes $5 \times 5$, $7.5 \times 7.5$, $10 \times 10$ and $10 \times 20$ cm. Nonwoven compresses are folded so as to consist of four layers. Thus, for the smallest size of folded sponge, $5 \times 5$ cm, there is a square having a total area in the unfolded state of $(5.5.4)^{\frac{1}{2}} \times (5.5.4)^{\frac{1}{2}} = 10 \times 10$ cm. The spinneret holes must accordingly have a spacing of no more than 10 cm, or, best, precisely 10 cm, at right angles to the machine direction (fleece production direction).

In a preferred embodiment of the process of the invention, the incorporation or distribution of the X-ray contrast medium into the sponge can also be performed indirectly. Prepolymer filaments containing contrast agent are extruded in a uniform or random distribution on cellulose or paper sheets. The sheets are then moistened with water in strips at an angle to the contrast filaments, so that moist and dry spots alternate on the filaments. In the moist areas the prepolymer cures, but not in the dry areas. At the end of the setting reaction, preferably accelerated by exposure to heat, several sheets containing no contrast medium, are treated in a pulper. At the hardened locations the cellulose fibrids are tightly bonded to the matrix polymer of the contrast filament, while little or no crosslinking takes place at the dry locations. As a result of poor bonding to the substrate fibers, the monofilament is easily broken up into fine particles in the pulper, while the sections of the sheets wetted with water contain the cylindrically shaped contrast medium as larger fragments.

A layer of fleece for the sponge is now deposited from a fiber suspension and dried, a weight of 12 to 15 $g/m^2$ being desirable. The fleece strips prepared as described above with small and larger fragments of the contrast medium are laid in the form of a discontinuous or continuous middle layer between card webs, resulting in a total weight of 35 to 50 g/m².

The sandwich is finally laid on a perforated mask and perforated with water jets. Drying and thermal consolidation then follow, in case binding fibers are contained in the cover fleeces and the perforation did not produce sufficient intertangling of the fibers.

The hydrodynamic treatment of the 3-layer sandwich causes the fibers both of the middle layer and of the outer layers to bond tightly at their points of contact with the new completely crosslinked polymer matrix of the contrast agent. If the middle fiber layer was applied discontinuously in the form of strips to form the support for the contrast medium, thicker areas containing these strips alternate with thinner areas containing no middle layer. This contruction results in a product having an especially good foldability along the thin areas.

The result is an especially high loft in the folded state and thus a greater capacity for the absorption of fluid as a result of the thickened areas.

Only the larger, cylindrical contrast medium particles have a sufficiently absorbing effect on X-rays.

The various features of novelty which characterize the invention are pointed out with particularity in the claims annexed to and forming a part of this specification. For a better understanding of the invention, its operating advantages and specific objects obtained by its use, reference should be had to the accompanying drawing and descriptive matter in which there is illustrated and described a preferred embodiment of the invention.

DESCRIPTION OF PREFERRED EMBODIMENT

Figure 1:
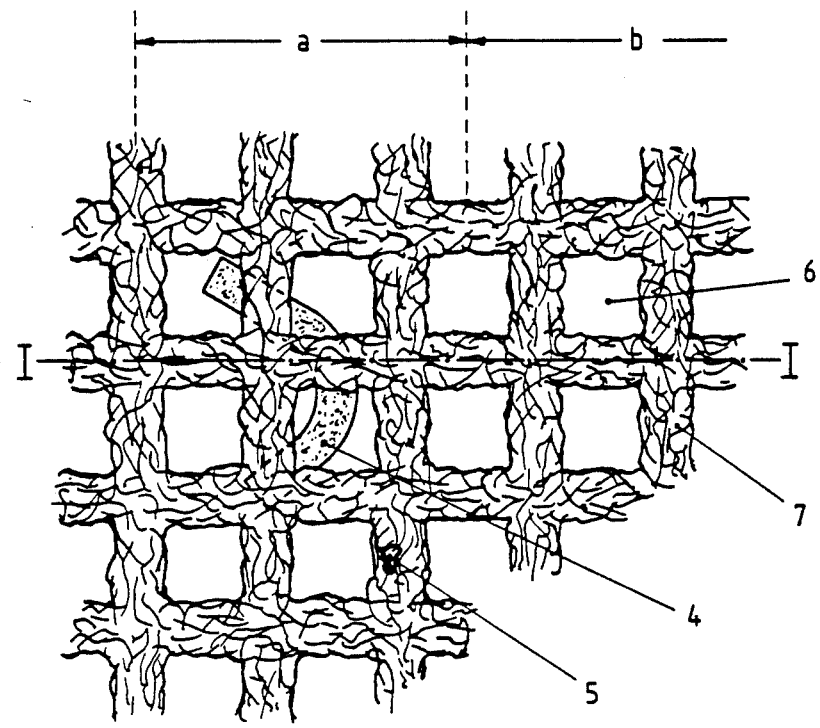
FIG. 1 shows a plan view of a sponge of the invention.
Figure 2:
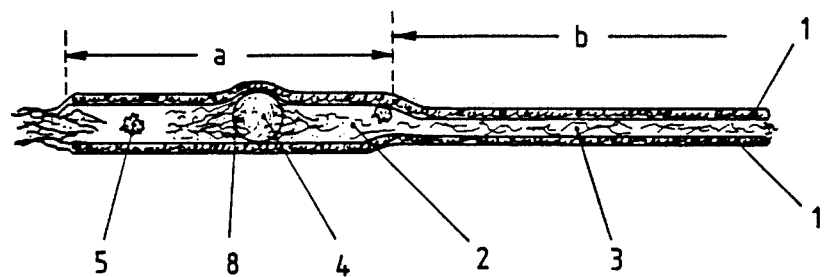
FIG. 2 is a cross section taken through the sponge along line I—I of FIG. 1.

Referring to the drawing, a fleece material, composed of two cover layers 1 and middle layers 2 and 3 containing the binding fibers, contains in the area a the wet fleece strip containing embedded X-ray contrast agent in the form of cylindrical bodies 4 and finely comminuted particles 5.

Contrast in the X-ray picture is produced only by the bodies 4 and the larger of the bodies 5. The areas a are thicker than the adjacent areas b.

The hydrodynamically created perforations 6 in the fiber framework 7 are preferably set in their shape by the action of heat after drying. The wet fleece staple fibers or cellulose fibrids 8 of the support strip are bound in the peripheral matrix of the cylindrical X-ray contrast agents 4. The protruding fibers are fixed by cellulose bonding and by thermal fiber consolidation to binding fibers of the middle layer 2. The alternating differences in thickness between the areas a and b result in an increase in the flexibility of the sponge and in better folding in and along the strips b. In the folded state the thicker areas a together produce an increase in the effective absorption volume.

In another embodiment of the process according to the invention, contrast threads are also incorporated in the sponge sandwich in the form of cylindrical fragments by extruding the contrast media as monofilaments parallel to one another onto water-soluble nonwoven or paper supports. The supports are then wetted on their entire surface with water until the prepolymer matrix is cured. Then the supports are cut up equidistantly at right angles to the monofilaments, treated in the pulper, deposited to form a sheet, and dried. The sheet, as described above, is laid between staple fiber card webs, and then the hydrodynamic perforation, drying and hot consolidation, if used, are performed.

The chemical treatment of a urethane prepolymer will be described below with the aid of two examples, a lengthening of the molecule chain being performed in the one case and a chemical crosslinking in the other.

EXAMPLE 1

(CHAIN LENGTHENING)

1 mole of a polyethylene oxide diglycol with a molecular weight of 2000 is added at 60° C. to 2 mole of hexamethylene diisocyanate. The mixture is stirred at 80° C. until an isocyanate content of 3.6 is reached.

The test for the isocyanate content is performed by a method described in "Polyurethanes, Chemistry, Technology and Properties", Phillips and Parker, Iliffe Books Ltd., London, p. 121–122 or DIN 53185 which is based on the reaction of the isocyanate groups with an amine to form the urea derivative. Aliphatic, secondary amines react rapidly with quantitatively with the NCO group to form trisubstituted ureas; if the dibutyl or diisobutyl amine is selected as the amine, the ureas that form are soluble in chlorobenzene in nearly all cases.

The determination is performed as follows:

The precisely weighed sample is dissolved in 10 ml of chlorobenzene in a 200-ml Erlenmeyer flask and an excess of 10 ml of a 1:10 n-dibutylamine solution in chlorobenzene is added. After the addition of about 50 ml of methanol, within 5 minutes the excess amine solution can be titrated with an n/10 hydrochloric acid solution against bromophenol blue (1% in ethanol) as indicator. The indicator will change from blue to yellow.

Computation:

$$\frac{(a-b) \times f \times 41.6}{E \times 10 \times 10} = -N = C = O(\%)$$

a = Consumption in ml of n/10 HCl for blind test
b = Consumption as above for principal test
f = Correction factor of the n/10 HCl, if HCl is not exactly n/10
E = Amount weighed in, in grams

Preparation Of X-ray Detectable Medium And Fixing On The Web

The polyurethane adduct based on hexamethylenediisocyanate had a melting point of approximately 35° C. It was heated up to a temperature of 60° C. The X-ray detectable, medical grade barium sulphate was added to the molten adduct and dispersed thoroughly. The viscosity after dispersing was 11,000 Centipoise measured with the Brookfield Viscosimeter at 50 UpM and spindle No. 6.

The mixture was poured into a heatable metal vessel ensuring that the temperature could be maintained at 60° C. constantly. The bottom was perforated in one single line with holes 'f 7 mm diameter. The distance between the holes was 20 mm.

The viscose liquid was pressed by its own weight through the die. After the adjustment of a constant flow rate a hydro-entangled, perforated nonwoven fabric of 45 g/sqm commonly used for surgical sponges, was moved with a speed equal to the impact speed of the monofilament on the web. The distance between the orifice and the nonwoven fabric was 30 cm. The diameter of the monofilament tapered from 7 mm at the die to approximately 0.5 mm on the nonwoven. The distance between the single monofilaments was 20 mm.

The connection between the fibers on the surgical sponge and the X-ray detectable medium was very strong because of its tackiness during impacting onto the nonwoven surface.

After a period of 12 hours storage at room temperature (23° C.) and 90% relative air humidity, the polyurethane matrix was crosslinked sufficiently, forming a linear, high-molecular weight, urea modified polyurethane, being elastic and resistant against steam sterilization.

EXAMPLE 2
(CROSSLINKING)

In a stirring vessel, 2 moles of diphenylmethane-4,4'-diisocyanate is added to an anhydrous mixture of 0.8 mole polyethylene oxide diol (average hydroxyl number 56) and 0.8 moles of polypropylene oxide triol (average hydroxyl number 35) at 60° C. Stirring is continued at 80° C. until an NCO content of 3.21% is reached.

By the method described, and its variants, a compress or a surgical sponge is obtained which is easy to fold repeatedly, which contains X-ray contrast material in sufficient amount to produce a clear contrast in the negative, and which can easily be sterilized by steam. The contrast medium is permanently bound to the body of the pad and its matrix can be extrudable even at low temperatures in a viscous liquid, adhesive state despite its absolute freedom from binding agent. The stated problem is thus completely solved.

A monofilament of barium sulphate and the crosslinkable aromatic prepolymer in ratio 50/50, with trifunctional isocyanate groups introduced by the triol component, is applied to the perforated hydroentangled fabric of Example 1 according to Example 1.

Due to the trifunctionality of the prepolymer, resulting in a tridimensional network after curing by means of water, the stability against steam sterilization is already attained after 6 hours at 23° C. and 90% rel. air moisture.

It will be understood that the specification and examples are illustrative but not limitative of the present invention and that other embodiments within the spirit and scope of the invention will suggest themselves to those skilled in the art.

We claim:

1. A process of making a surgical sponge of fibrous nonwoven fabric containing cellulose fibers and a nonthermoplastic matrix material, said matrix material containing a material which is impervious to X-rays, comprising the steps of:
    extruding onto a surface of a moving nonwoven fabric containing a majority of cellulosic fibers a prepolymer of a nonthermoplastic matrix material containing at least 40% by weight of a material which is impervious to X-rays, said prepolymer having chemically reactive groups and said prepolymer furthermore being free of plasticizing agents;
    polymerizing said prepolymer into a soft, elastic and flexible matrix material so as to embed said cellulosic fibers in said matrix material; and
    consolidating said polymer-containing fibrous nonwoven fabric.

2. The process of claim 1 wherein the prepolymer is an oligomer organic acrylate system which can be cross liked by wave radiation.

3. The process of claim 1 wherein the consolidation is by fiber entanglement.

4. The process of claim 1 wherein the consolidation is by fiber fusion.

5. The process of claim 1 wherein the prepolymer polymerizes by cross linkage.

6. The process of claim 1 wherein the prepolymer polymerizes by chain elongation.

7. The process of claim 1 wherein the prepolymer is an oligomer organic acrylate system which can be cross linked by particle radiation.

8. The process of claim 1 wherein the X-ray impervious material is extruded as an endless monofilament onto the surface of the nonwoven fabric.

9. The process of claim 1 wherein the prepolymer is a urethane oligomer with a molecular weight between 168 and 20,000 and with 2 to 5 free isocyanate groups per 168 and 20,000 and with 2 to 5 free isocyanate groups per molecule and that the latter is reacted with water in excess under the formation of urea.

10. The process of claim 9 wherein the oligomer has a molecular weight between 1200 and 8000.

11. The process of claim 9 wherein said polymer-containing nonwoven fabric is consolidated by fiber entanglement, comprising the steps of:
    applying water to said polymer-containing nonwoven fabric by water jets;
    removing excess water; and
    allowing residual water to react with the isocyanate groups of said urethane oligomer under heat to completely polymerize and cure said matrix material.

* * * * *